United States Patent [19]

Kuratsune et al.

[11] Patent Number: 5,576,348
[45] Date of Patent: Nov. 19, 1996

[54] PHARMACEUTICAL PREPARATION COMPRISING AN ACYLCARNITINE

[76] Inventors: Hirohiko Kuratsune, 3-2-10, Kamishinden, Toyonaka-shi; Teruo Kitani, 28-15, Fujishirodai 2-chome, Suita-shi, both of Osaka 565, Japan

[21] Appl. No.: 438,969

[22] Filed: May 11, 1995

[30] Foreign Application Priority Data

May 12, 1994 [JP] Japan .................................. 6-124438

[51] Int. Cl.⁶ .................................................. A61K 31/225
[52] U.S. Cl. ............................................................. 514/547
[58] Field of Search ............................................. 514/547

[56] References Cited

FOREIGN PATENT DOCUMENTS

0516594A1 12/1992 European Pat. Off. .
0517125A1 12/1993 European Pat. Off. .

*Primary Examiner*—Phyllis G. Spivack
*Attorney, Agent, or Firm*—Wenderoth, Lind & Ponack

[57] ABSTRACT

A method for treating Acylcarnitine Metabolic Dysfunction Syndrome comprising administering an acylcarnitine or a pharmacologically acceptable salt thereof orally or parenterally is disclosed. The acylcarnitine may be acetylcarnitine, propionylcarnitine, butyrylcarnitine, isobutyrylcarnitine, valerylcarnitine, isovalerylcarnitine or hexanoylcarnitine.

4 Claims, No Drawings

5,576,348

PHARMACEUTICAL PREPARATION COMPRISING AN ACYLCARNITINE

BACKGROUND OF THE INVENTION

1. Field of the Invention

The present invention relates to a pharmaceutical preparation for therapy of a patient suffering from a symptom caused by acylcarnitine metabolic dysfunction, or for improvement or prophylaxis of such symptom.

2. Description of Related Art

The majority of energy supply for human cells is generated in the mitochondrial glycolysis and fatty acid metabolism. In such energy metabolism, carnitine plays some important roles. That is, although being the major source of the energy supply, a long-chain fatty acid itself can not pass through the inner mitochondrial membrane, and hence free carnitine is required in the transfer of the long-chain fatty acid across the mitochondrial membrane. Further, the free carnitine has another important role. Namely, when a short-chain fatty acid-CoA/CoA ratio is increased by, for example, enhanced glycolysis or heat generation through exercise, the activities of numerous enzymes such as pyruvate dehydrogenase and branched-chain ketoacid dehydrogenase are inhibited, and the free carnitine has a function or activity of inhibiting or suppressing such abnormal increase of the short-chain fatty acid-CoA (coenzyme A) produced by β-oxidation of a fatty acid and of preventing increase of an acetyl-CoA caused by enhanced glycolysis to maintain the short-chain fatty acid-CoA/CoA ratio in a constant range.

Decrease of the free carnitine having such important roles in the energy metabolism is expected to cause cellular dysfunction or cellular abnormality. Indeed, aiming at the functions of free carnitine which does not bond with a fatty acid, it has been reported that primary and/or secondary carnitine deficiency cause a lot of neuro-muscular symptoms. Such carnitine deficiency is defined as a decrease of the intracellular free carnitine level or total carnitine level which is the sum of the free carnitine and acyl-binding carnitines. It has also been reported that administration of free carnitine is a useful treatment to a patient suffering from such symptom.

As mentioned above, the physiological roles of the free carnitine have been well studied in the world and the administration of the free carnitine is clearly established as a treatment for carnitine deficiency. However, as for the acylcarnitine, i.e. a carnitine binding with a fatty acid, most of investigators think that the acylcarnitine might be nothing but a temporary substance in the long-chain fatty acid uptake to the mitochondria. In fact, it is reported that the serum acylcarnitine discharged from mitochondria is excreted to urine, and that reabsorption ratio of the acylcarnitine is lower than that of the free carnitine, and therefore, in the usual state, the free carnitine concentration in serum is several times as high as the acylcarnitine concentration, but in urine, the acylcarnitine concentration is higher than the free carnitine concentration. Accordingly, little attention has been paid to the in vivo physiological and biochemical roles of the serum acylcarnitine itself at present.

In EP-A1-0517125 corresponding to Japanese Patent Application Laid-open No. 155766/1993 (JP-A-5-155766), a pharmaceutical composition containing an acyl-L-carnitine is disclosed. The pharmaceutical composition is, however, used in order to recover the decreased muscular tonus (myotony) of a patient immobilized for a long period because of the fixation of the limbs due to bone fracture.

EP-A1-0516594 corresponding to Japanese Patent Application Laid-open No. 148200/1993 (JP-A-5-148200 discloses the use of an acyl-L-carnitine, especially isovaleryl-L-carnitine, as a therapeutic agent only for the treatment of the muscular disturbance (myopathy), degenerative diseases of nerves (for example, Alzheimer's senile dementia and so on) and for the inhibition of proteolysis in liver, skeletal muscle and cardiac muscle. However, the symptoms, to which these therapeutic agents are applied, are quite different from those caused by or related with the metabolic dysfunction of the acylcarnitine.

SUMMARY OF THE INVENTION

It is an object of the present invention to provide a pharmaceutical preparation useful for therapy (treatment) or prophylaxis of a patient suffering from Acylcarnitine Metabolic Dysfunction Syndrome (hereinafter may be referred to as ACMDS) who has a symptom caused by the metabolic dysfunction of an acylcarnitine.

Another object of the present invention is to provide a pharmaceutical preparation whereby various symptoms related with Acylcarnitine Metabolic Dysfunction Syndrome can effectively be improved or prevented with high efficiency.

After the investigations in the physiological roles of an acylcarnitine (a carnitine binding with a fatty acid), the present inventors found that such acylcarnitine is not discharged into the urine as a mere disuse or unnecessary substance. Further, when they investigated the acylcarnitine metabolism in the body in Rhesus monkey by positron emission tomography (PET) using [$^{11}$C]-acetyl-L-carnitine, they found that one of the acyl carnitine, in usual state, [$^{11}$C]-acetyl-L-carnitine was taken up to kidney in a physiological concentration, but urinary excretion of the acetyl-carnitine was very low of less than 1% after 2 hours of [$^{11}$C]-acetyl-L-carnitine administration (injection) and such [$^{11}$C]-acetyl- L-carnitine was taken up to skeletal muscles, cardiac muscles, liver, pancreas, brain, kidney and blood cells. They also found that acylcarnitine was used not only for producing the acetyl-CoA to make an energy, but also for providing the acetyl- and methyl-radicals (groups) for the various metabolisms in many tissues (for example, skeletal muscle, cardiac muscles, liver, pancreas, brain, kidney, blood cells, etc.). Furthermore, they found the possibilities that acylcarnitine has more important physiological roles by taken up into various tissues in place of fatty acids and saccharides (glucose) under the disturbance of usual fatty acids and saccharides metabolism caused by various causes (for example, stress, mental and physical fatigue, infections, malignancies (malignant tumors), autoimmune diseases, chronic fatigue syndrome, endocrine diseases, thrombosis, embolism, etc.). They also found that various modes of diseases are caused by the acylcarnitine metabolic dysfunction and such diseases are quite different from those of primary and/or secondary carnitine deficiency reported previously. Further, they found that the ACMDS is caused by extremely various types of diseases and a variety of symptoms are raised by ACMDS regardless of the cause of ACMDS itself, and that the administration of an acylcarnitine or a salt thereof is useful for therapy (treatment) and/or prophylaxis (prevention) of such modes of diseases. The present invention has been accomplished based on these findings.

Thus, the pharmaceutical preparation of the present invention comprises an acylcarnitine or a pharmacologically acceptable salt thereof for therapy or prophylaxis of a symptom caused by the metabolic dysfunction of an acylcarnitine. The acylcarnitine may be, for example, acetylcarnitine, propionylcarnitine, butyrylcarnitine, isobutyrylcarnitine, valerylcarnitine, isovalerylcarnitine, hexanoylcarnitine and the like. The pharmaceutical preparation may be administrable orally or parenterally.

DETAILED DESCRIPTION OF THE INVENTION

In this specification, the term "a symptom caused by acylcarnitine metabolic dysfunction" may occasionally referred to as a symptom or disease related with Acylcarnitine Metabolic Dysfunction Syndrome or may be simply referred to as "ACMDS".

The pharmaceutical preparation of the present invention comprising an acylcarnitine is applied to the treatment (therapy) and/or prophylaxis of a patient suffering from various symptoms caused by or related with the acylcarnitine metabolic dysfunction or a human (patient) being going to suffer from such symptom, to the amelioration (improvement), relief and/or prevention of such symptoms, and is useful for the recovery of the decreased cellular functions due to such symptoms. The pharmaceutical preparation comprising an acylcarnitine may also be applied to a human being (patient) having a possibility of decreased serum acylcarnitine or being going to suffer from a symptom caused by acylcarnitine metabolic dysfunction such as a human being (patient) having, for example, a cause which may cause ACMDS as mentioned hereinafter for preventing or suppressing the occurring or manifesting of such symptom. The symptoms and diseases manifesting related with Acylcarnitine Metabolic Dysfunction Syndrome are characterized by the serum acylcarnitine deficiency without serum free carnitine deficiency. In such symptoms and diseases, the serum free carnitine may frequently be in the normal range. Meanwhile, by determination using the enzyme cycling method (Takahashi M. et al., Clin. Chem., 38, 958–959 (1992)), the normal range of serum free carnitine is about 45 to 67 μmol/L for male and about 33 to 54 μmol/L for female, and the normal range of the serum acylcarnitine is about 9 to 18 μmol/L for male and about 11 to 20 μmol/L for female. The manifestation of the condition of the disease in Acylcarnitine Metabolic Dysfunction Syndrome seems to be closely related with mitochondrial metabolic dysfunction of an acylcarnitine.

It is reported that serum acylcarnitine concentration in a patient suffering from chronic fatigue syndrome (CFS) having basic symptoms such as prolonged general fatigue (malaise), slight fever (febricula), lymphadenopathy, myalgia, arthralgia and neuropsychiatric symptoms is lower than that in a normal control, while the free carnitine concentration in serum in CFS is in the normal range (The Journal of Clinical Science (Rinsho Kagaku), 29, 6, 663–668 (1993) and Clinical Infectious Disease, 18 (suppl. 1), /S62–S67 (1994)). However, it is not yet known that administration of an acylcarnitine or a salt thereof is effective for the treatment and/or prevention not only for a patient suffering from chronic fatigue syndrome but also for a patient with a symptom or disease caused by the acylcarnitine metabolic dysfunction.

As causes of ACMDS, there may be mentioned, for example, physical or psychological fatigue, stress, infections (for instance, caused by virus, bacteria, fungi, richettsia, protozoans, etc.), dysfunction or abnormality caused by cytokines (for example, interferon-α, -β, -γ, interleukin-1 (IL-1), interleukin-2, (IL-2), tumor necrosis factor α (TNFα) and so on), malignant tumors, endocrine diseases, various types of metabolic disturbances, immunological abnormalities such as autoimmune diseases, chronic fatigue syndrome (CFS), chronic inflammatory diseases, thrombosis, embolism, neuro-muscular diseases, psychiatric diseases, drug abuse, toxicosis (poisoning) and others. When being complicated with ACMDS, the patient has further symptoms caused by ACMDS in addition to symptoms of the basal disease. Whereas a clear understanding of ACMDS has not been established for the present, such further symptoms related with or added by ACMDS are thought to be a series of symptoms accompanied with the basal disease.

Examples of the symptoms and signs (diseases) related with or caused by ACMDS include symptoms related with general or systemic cellular dysfunction such as general fatigue (malaise), headache, arthralgia, low grade fever (febricula), sleep disturbance (somnipathy) such as hypersomnia and insomnia, vertigo, neuropsychologic complaints or symptoms such as photophobia, visual scotomata, forgetfulness (amnesia), excessive irritability, confusion, difficulty of thinking, inability to concentrate (aprosexia), sensory disturbance, dyskinesia (motor paralysis, ataxia, etc.), depression and so on, loss of appetite (anorexia), eye strain (dimmed eye) or dry eye, gastro-enterological symptoms (for instance, abdominal pain, nausea, diarrhea, constipation and the like), dry mouth (thirst), night sweat, respiratory symptoms (cough, dyspnea, shortness of breath, sore throat, chest pain and so on), circulatory symptoms (arrhythmia, tachycardia, bradycardia, palpitation, pectoralgia, shock, blood pressure abnormalities such as hypertension, hypotension, etc.), urinary frequency (thamuria), oliguria, exanthema, dysfunction of white blood cells (decrease of natural killer cell activity, dysfunction of lymphocytes, dysfunction of monocytes and others) and abnormal red blood cell shape.

The cause of serum acylcanitine deficiency in a patient suffering from ACMDS are not clarified, and there are may possibilities such as the following explanations.

(i) A sufficient amount of carnitine cannot be obtained from food, and (ii) the insufficiency or lack of the carnitine synthesis in the liver or kidney.

However, these two explanations are denied because the patient suffering from ACMDS has normal free-L-carnitine concentration. Accordingly, the possibilities are as follows:

(iii) a carnitine acyltransferase-1 (CAT-1) deficiency, (iv) disturbance of the mitochondrial β-oxidation of a fatty acid, (v) disturbance or disorder of the binding of an acetyl-CoA with the carnitine, wherein such acetyl-Coa is produced by metabolism in the glycolysis system or β-oxidation of a fatty acid, dysfunction or abnormality of transfer of the short-chain fatty acid-CoA to a short-chain fatty acid carnitine (acylcarnitine) in the mitochondria, and/or decrease of the production of the short-chain fatty acid-CoA in the fatty acid metabolic system, (vi) mitochondrial dysfunction such that the acylcarnitine cannot path through the mitochondrial inner membrane sufficiently, and (vii) accumulation or uptake of the serum acylcarnitine into other tissue or organ.

In the patient with Acylcarnitine Metabolic Dysfunction Syndrome, the amount of the free carnitine discharged to the urine is not increased in comparison with a normal control, and the analysis of the acylcarnitine profiles of the urine is also normal. Therefore, the serum acylcarnitine deficiency in the patient with ACMDS seems not to correlate with the loss of the acylcarnitine to the urine.

The pharmaceutical preparation of the present invention comprises an acylcarnitine or a pharmacologically acceptable salt thereof. As the acylcarnitine, there may be mentioned, for instance, a carnitine having a straight-chain or branched-chain acyl group having about 2 to 12 carbon atoms such as acetylcarnitine, propionylcarnitine, butyrylcarnitine, isobutyrylcarnitine, valerylcarnitine, isovalerylcarnitine, pivaloylcarnitine, hexanoylcarnitine, lauroylcarnitine and so forth.

Preferred examples of the acylcarnitine include an acylcarnitine containing an acyl group having about 2 to 6 carbon atoms (preferably about 2 to 4 carbon atoms), specifically acetylcarnitine and propionylcarnitine, and acetylcarnitine can advantageously be employed among others. These acylcarnitines may be used singly or in combination.

The acylcarnitine may form an inner salt or a pharmacologically acceptable salt with an acid. Such acid which forms a pharmacologically acceptable salt includes, for example, an inorganic acid such as hydrochloric acid, hydrobromic acid, sulfuric acid, nitric acid, a phosphoric acid and a boric acid; an organic acid such as formic acid, acetic acid, propionic acid, trifluoroacetic acid, oxalic acid, succinic acid, maleic acid, fumaric acid, lactic acid, malic acid, tartaric acid, citric acid, salicylic acid, gallic acid, aspartic acid, methanesulfonic acid, trifluoromethanesulfonic acid, benzenesulfonic acid, p-toluenesulfonic acid and the like. Such salts may be employed singly or in combination.

The acylcarnitine or a salt thereof has higher therapeutic and/or prophylactic activities (effects) on the signs or diseases, symptoms and cellular dysfunctions manifesting accompanied or related with Acylcarnitine Metabolic Dysfunction Syndrome. Therefore, the administration of the acylcarnitine or a salt thereof can cause the increase of serum and cellular acylcarnitine concentration to modulate or control the intramitochondrial acyl-CoA/CoA ratio, and not only the energy but also acetyl group and/or methyl group can be supplied to various cells such as brain cells, skeletal muscles, cardiac muscles, liver, pancreas, kidney and so on. Accordingly, by such administration, Acylcarnitine Metabolic Dysfunction Syndrome can effectively be treated and/or prevented. Further, the acylcarnitine or a salt thereof has lower toxicity and thus higher safety, and therefore, the acylcarnitine or its salt can be used as a safety therapeutic and/or prophylactic agent for a mammalian animal such as a human being.

The acylcarnitine may be administered as intact. The content of the acylcarnitine or a salt thereof in the whole pharmaceutical preparation is not specifically restricted and can be selected from such a range as similar to those of common pharmaceutical preparations, and may, for example, be about 10 to 90% by weight, in terms of the acylcarnitine, based on the total weight of the pharmaceutical preparation. The dose of the acylcarnitine or a salt thereof depends upon the species of the acylcarnitine, route of administration, age of the patient to be treated, species and extent of the disease in Acylcarnitine Metabolic Dysfunction Syndrome, and the dose in oral administration to an adult human may usually be about 0.1 to 30 g per day, preferably about 1 to 10 g per day and frequently about 2 to 6 g per day. The dosage time per day is not strictly limited and the pharmaceutical preparation may be administered once a day as well as in plural doses or several times daily. The pharmaceutical preparation of the present invention can be administered orally or parenterally (e.g. suppositories, hypodermic injection, intramuscular injection, intravenous injection, etc.).

The dosage form of the pharmaceutical preparation includes, for example, solid preparations such as tablets, powders, fine granules, granules, pills, suppositories, capsules and so on; liquid preparations such as solutions, suspensions, emulsions, syrups, injections, transfusions and others.

When the pharmaceutical preparation is formulated into a solid pharmaceutical preparation for oral administration, a conventional component can be used. Examples of such component include excipients such as saccharides including Starch (e.g. corn starch), lactose, sucrose, mannitol and the like, crystalline cellulose, carboxymethylcellulose and silicic acid; binders such as poly(vinyl alcohol), poly(vinylpyrrolidone), poly(vinyl ether), ethylcellulose, hydroxypropylcellulose, gum arabic, tragacanth, gelatin, dextrin, pectin and so forth; lubricants such as magnesium stearate, talc and polyethylene glycol; disintegrators such as carboxymethylcellulose calcium; disintegrating-auxiliaries; stabilizers; colorants and so on.

In formulating the pharmaceutical preparation into a liquid preparation, a conventional component depending on the species of such liquid preparation may be employed. As such component, there may be mentioned, for example, water, ethyl alcohol, ethylene glycol, glycerol, surfactants such as polyoxyethylene-sorbitan fatty acid esters, glucose, amino acids, soothing agents, solubilizing agents, buffers, colorants, preservatives, sweeteners and others.

The pharmaceutical preparation in such dosage form may be prepared by using the acylcarnitine or a salt thereof and, if necessary, the additive component as mentioned above, according to a conventional manner such as granulation including fluidizing-granulation, tumbling-granulation, spray-granulation and the like, mixing, sterilization and so forth.

The pharmaceutical preparation of the present invention which comprises the acylcarnitine or a salt thereof is useful for the therapy and/or prevention (prophylaxis) of the symptoms caused by or related with the metabolic dysfunction of the acylcarnitine. Further, use of the pharmaceutical preparation comprising an acylcarnitine having an acyl group containing 2 to 4 carbon atoms or a pharmacologically acceptable salt thereof, or the pharmaceutical preparation administrable orally or parenterally can effectively be used to treat and/or prevent various symptoms related with Acylcarnitine Metabolic Dysfunction Syndrome with high efficiency.

The following examples are intended to describe this invention in further detail and should by no means be construed as defining the scope of the invention.

EXAMPLES

In the examples, the measurement of free carnitine and acylcarnitine was conducted according to the enzymatic cycling method (Takahashi M. et al., Clin. Chem. 38, 958–959 (1992)).

EXAMPLE 1

(1) As being the main component of serum acylcarnitines in human, acetylcarnitine was employed as the acylcarnitine, and the acetyl group of the acetylcarnitine was labeled with a radioisotope ($^{11}C$). The labeled acetylcarnitine was administered intravenously to 2 monkeys, and the kinetic of the acetylcarnitine in vivo was investigated using positron emission tomography (PET). As a control, a radioisotope ($^{11}C$)-labeled acetic acid was used.

As a result, the radioisotope ($^{11}C$)-labeled acetic acid rapidly disappeared from the blood and scarcely taken up into the brain. To the contrary, about 14.4% by weight of the [$^{11}C$]-labeled acetylcarnitine remained in blood even after 40 minutes from the administration, and less than 1% by weight of the acylcarnitine was excreted to urine after two hours from the administration. Most of the [$^{11}C$]-acetyl-L-carnitine was accumulated into the kidney, and some of them was accumulated into the pancreas, cardiac muscle and liver. About 12.7% by weight and about 0.8% by weight of the administered [$^{11}C$]-acetyl-L-carnitine were taken up into the muscular tissue and the brain tissue, respectively.

(2) The physiological meanings or roles of the acylcarnitine were investigated by determining the increase of the blood acylcarnitine level by oral administration. That is, by using acetylcarnitine as the acylcarnitine and 3 healthy humans as the subjects, 2 g of acetylcarnitine was administered respectively to the subjects in the early morning when hungry before a meal. Resultantly, the concentration of the acylcarnitine was increased after 1 hour from the administration, and the concentration after 3 hours from the administration was increased by a factor of 25.3% on the average in comparison with the concentration before the administration.

Meanwhile, to 5 patients suffering from ACMDS, acetylcarnitine was administered orally in the same manner as above. Resultantly, after 1 to 3 days from the initial of the administration, the symptoms were observed to be improved.

(3) Five patients suffering from ACMDS were administered respectively with 4 g per day (2 g per single dosage, twice a day; after meal in the morning and in the evening) of acetylcarnitine for 14 days. The activity of natural killer cell (NK cell) was determined as an index of the change of immune activity after the administration compared with that of before administration. As a result, significant increase of the natural killer cell activity due to the administration of acetylcarnitine was recognized as follows.

NK cell activity before the administration:

E:T=10:1, 15.6±7.3%,

E:T=20:1, 26.9±11.0%

NK cell activity after the administration:

E:T=10:1, 29.4±11.0%,

E:T=20:1, 44.3±22.6%

(4) Acetylcarnitine was administered orally to 5 patients suffering from ACMDS respectively in a dose of 4 g per day (2 g per single dosage, twice a day; after meal in the morning and in the evening) for 14 days and the change of the clinical symptoms or remarks was investigated.

As a result, in the 2nd day from the initial of the administration, in some cases, systemic malaise, febricula, myalgia, arthralgia, neuropsychologic complains or symptoms (difficulty of concentration, decrease of thinking faculty, etc.) were observed to be improved. In the 14th day from the initial of the administration, all of the 5 cases were observed to be improved in the clinical symptoms. Accompanying with the interruption of the administration, some cases were observed that the symptoms which had been once improved were deteriorated or worsened to return to the state before the administration.

PREPARATION EXAMPLE 1

To 77 parts by weight of lactose, were added 10 parts by weight of hydroxypropylcellulose, 1 part by weight of light silicic anhydride, 2 parts by weight of magnesium stearate and 10 parts by weight of acetylcarnitine, and the mixture was blended homogeneously. The resultant mixture was compression-molded to give a tablet.

PREPARATION EXAMPLE 2

A capsule was filled with the resultant mixture obtained in Preparation Example 1 to give a capsule.

What is claimed is:

1. A method of treating a symptom in a patient suffering from Acylcarnitine Metabolic Dysfunction Syndrome caused by acylcarnitine metabolic dysfunction, which comprises administering orally or parenterally a therapeutically effective amount of an acylcarnitine or a pharmacologically acceptable salt thereof to a patient in need thereof, wherein said patient has a decreased serum acylcarnitine level without a decreased serum free carnitine level.

2. The method according to claim 1, wherein said acylcarnitine is at least one member selected from the group consisting of acetylcarnitine, propionylcarnitine, butyrylcarnitine, isobutyrylcarnitine, valerylcarnitine, isovalerylcarnitine and hexanoylcarnitine.

3. The method according to claim 1, wherein said acylcarnitine is an acylcarnitine having a straight-chain or branched-chain acyl group having 2 to 4 carbon atoms or a pharmacologically acceptable salt thereof.

4. The method according to claim 1, wherein the acylcarnitine or pharmacologically acceptable salt is administered to the patient in a pharmaceutical preparation comprising acetylcarnitine or a pharmacologically acceptable salt thereof, and wherein the patient has a decreased serum acylcarnitine level of less than the normal range of 9 to 18 mmol/L for male and 11 to 20 mmol/L for female and has a serum free carnitine level within the normal range of 45 to 67 mmol/L for male and 33 to 54 mmol/L for female.

* * * * *